(12) United States Patent
Hirvonen et al.

(10) Patent No.: US 11,426,238 B2
(45) Date of Patent: Aug. 30, 2022

(54) AUTOMATED SYSTEM FOR LASER-ASSISTED DERMATOLOGICAL TREATMENT

(71) Applicant: Cryotech Nordic AS, Harju maakond (EE)

(72) Inventors: Vesa Hirvonen, Espoo (FI); Jan Eklund, Vantaa (FI); Juha Tapani Yliollitervo, Jarvenpaa (FI)

(73) Assignee: CRYOTECH NORDIC AS, Harju Maakond (EE)

( * ) Notice: Subject to any disclaimer, the term of this patent is extended or adjusted under 35 U.S.C. 154(b) by 312 days.

(21) Appl. No.: 16/655,583

(22) Filed: Oct. 17, 2019

(65) Prior Publication Data

US 2020/0046427 A1 Feb. 13, 2020

Related U.S. Application Data

(63) Continuation of application No. 15/337,112, filed on Oct. 28, 2016, now abandoned.

(30) Foreign Application Priority Data

Nov. 2, 2015 (FI) .................................. 20155784

(51) Int. Cl.
*A61B 18/20* (2006.01)
*A61N 5/06* (2006.01)
(Continued)

(52) U.S. Cl.
CPC .......... *A61B 18/203* (2013.01); *A61B 18/201* (2013.01); *A61B 34/10* (2016.02);
(Continued)

(58) Field of Classification Search
None
See application file for complete search history.

(56) References Cited

U.S. PATENT DOCUMENTS 6,165,170 A 12/2000 Wynne et al.
6,887,233 B2 5/2005 Angeley
(Continued)

FOREIGN PATENT DOCUMENTS

WO 2011/004285 1/2011

OTHER PUBLICATIONS

FI Search Report, dated May 12, 2016, from corresponding FI application.
(Continued)

*Primary Examiner* — Carl H Layno
*Assistant Examiner* — Manolis Pahakis
(74) *Attorney, Agent, or Firm* — Nixon & Vanderhye

(57) ABSTRACT

A system for automated laser-assisted dermatological treatment is provided, the system comprises a robot arm assembly, comprising a laser head coupled to the robot arm and a controlling unit. The system is configured to remove an undesirable dermatological condition from skin by directing laser energy to a pre-defined skin surface area intended for treatment essentially in an absence of human attendance. A method for real-time controlling an automated laser-assisted removal of undesirable dermatological condition from skin implemented by a system and a computer program product for causing the computer to execute the method are further provided.

11 Claims, 6 Drawing Sheets

(51) Int. Cl.
*A61B 34/10* (2016.01)
*A61B 34/00* (2016.01)
*A61B 34/30* (2016.01)
*A61B 90/00* (2016.01)
*A61B 18/00* (2006.01)
*A61N 5/067* (2006.01)
*A61B 17/00* (2006.01)

(52) U.S. Cl.
CPC ............. *A61B 34/25* (2016.02); *A61B 34/30* (2016.02); *A61B 90/361* (2016.02); *A61N 5/0616* (2013.01); *A61B 2017/00022* (2013.01); *A61B 2018/00452* (2013.01); *A61B 2018/00458* (2013.01); *A61B 2018/00636* (2013.01); *A61B 2018/2025* (2013.01); *A61B 2018/20351* (2017.05); *A61B 2034/105* (2016.02); *A61B 2090/367* (2016.02); *A61N 5/067* (2021.08)

(56) References Cited

U.S. PATENT DOCUMENTS

| | | | |
|---|---|---|---|
| 7,108,690 B1 | 9/2006 | Lefki | |
| 7,469,160 B2* | 12/2008 | Banks | A61B 5/0059 600/123 |
| 7,586,957 B2 | 9/2009 | Sierra et al. | |
| 7,652,259 B2* | 1/2010 | Kimchy | A61B 1/05 250/370.08 |
| 7,720,306 B2 | 5/2010 | Gardiner | |
| 7,929,579 B2 | 4/2011 | Hohm et al. | |
| 7,993,289 B2* | 8/2011 | Quistgaard | A61B 8/00 601/2 |
| 8,182,473 B2 | 5/2012 | Altshuler | |
| 8,187,256 B2 | 5/2012 | Smits et al. | |
| 8,565,860 B2* | 10/2013 | Kimchy | A61B 5/07 600/436 |
| 9,245,374 B2* | 1/2016 | McQueston | G06T 15/08 |
| 9,345,552 B2* | 5/2016 | Janik | A61B 34/75 |
| 9,743,988 B2* | 8/2017 | Tenney | A61B 34/30 |
| 10,004,530 B2* | 6/2018 | Zingaretti | A61B 34/30 |
| 2001/0053907 A1 | 12/2001 | Ota | |
| 2002/0065461 A1 | 5/2002 | Cosman | |
| 2002/0193685 A1* | 12/2002 | Mate | A61N 5/1049 600/424 |
| 2003/0060810 A1 | 3/2003 | Syrowicz et al. | |
| 2003/0192557 A1* | 10/2003 | Krag | A61B 34/20 128/898 |
| 2003/0236487 A1* | 12/2003 | Knowlton | A61B 18/203 604/20 |
| 2004/0206365 A1* | 10/2004 | Knowlton | A61B 18/14 128/898 |
| 2006/0142657 A1* | 6/2006 | Quaid | A61F 2/30942 600/424 |
| 2006/0207978 A1* | 9/2006 | Rizun | A61B 34/76 219/121.83 |
| 2006/0279698 A1 | 12/2006 | Muhlhoff | |
| 2007/0156047 A1* | 7/2007 | Nagler | A61B 6/00 600/436 |
| 2007/0236514 A1* | 10/2007 | Agusanto | G16H 50/50 345/646 |
| 2008/0033410 A1 | 2/2008 | Rastegar et al. | |
| 2008/0033420 A1 | 2/2008 | Nields | |
| 2008/0051773 A1 | 2/2008 | Ivanov et al. | |
| 2008/0171930 A1 | 7/2008 | Abolfathi | |
| 2008/0172112 A1* | 7/2008 | Gourgouliatos | A61N 5/0617 607/94 |
| 2008/0172115 A1* | 7/2008 | Gourgouliatos | A61N 5/0617 607/94 |
| 2008/0188839 A1 | 8/2008 | Chan | |
| 2008/0247637 A1* | 10/2008 | Gildenberg | A61B 18/203 382/153 |
| 2009/0043556 A1* | 2/2009 | Axelson | G06F 30/00 600/416 |
| 2009/0131922 A1 | 5/2009 | Dewey | |
| 2009/0306498 A1 | 12/2009 | Bodduluri | |
| 2010/0114080 A1 | 5/2010 | Theriault | |
| 2010/0168586 A1* | 7/2010 | Hillman | A61B 5/445 600/476 |
| 2010/0185087 A1 | 7/2010 | Nields | |
| 2010/0191124 A1* | 7/2010 | Prokoski | G01K 13/20 600/473 |
| 2010/0234871 A1* | 9/2010 | Qureshi | G06T 7/0012 606/187 |
| 2010/0277571 A1* | 11/2010 | Xu | G06T 17/00 348/47 |
| 2010/0312096 A1 | 12/2010 | Guttman | |
| 2011/0028212 A1* | 2/2011 | Krien | A63F 13/655 463/32 |
| 2011/0083696 A1* | 4/2011 | Nasr | H01L 21/67028 134/1.1 |
| 2011/0137156 A1* | 6/2011 | Razzaque | A61B 18/1477 600/424 |
| 2011/0166560 A1 | 7/2011 | Kuo | |
| 2011/0189440 A1* | 8/2011 | Appleby | B22C 9/10 523/435 |
| 2011/0218597 A1 | 9/2011 | Wang | |
| 2012/0071794 A1* | 3/2012 | Karni | A61B 34/30 601/2 |
| 2012/0116417 A1* | 5/2012 | Bodduluri | A61B 34/32 606/130 |
| 2012/0141949 A1* | 6/2012 | Bodony | G01B 11/25 433/29 |
| 2012/0158019 A1* | 6/2012 | Tenney | A61B 34/10 606/133 |
| 2012/0253331 A1 | 10/2012 | Liu et al. | |
| 2013/0060146 A1* | 3/2013 | Yang | G01B 11/24 600/476 |
| 2013/0190776 A1* | 7/2013 | Zhang | A61B 34/30 606/133 |
| 2013/0261446 A1* | 10/2013 | Paladini | A61B 6/4417 600/436 |
| 2013/0274582 A1 | 10/2013 | Afonso | |
| 2013/0345718 A1* | 12/2013 | Crawford | A61B 90/39 606/130 |
| 2014/0005523 A1* | 1/2014 | Kohler | G01R 33/4804 600/411 |
| 2014/0052555 A1* | 2/2014 | MacIntosh | G07G 1/12 705/23 |
| 2014/0067024 A1 | 3/2014 | Jones | |
| 2014/0188128 A1 | 7/2014 | Weber | |
| 2014/0261467 A1 | 9/2014 | Zhang | |
| 2014/0270480 A1* | 9/2014 | Boardman | G06T 17/00 382/154 |
| 2014/0276200 A1* | 9/2014 | Brannan | A61B 18/1815 600/562 |
| 2014/0296978 A1* | 10/2014 | Boyden | A61B 5/14546 623/8 |
| 2014/0350571 A1 | 11/2014 | Maillet | |
| 2015/0049081 A1 | 2/2015 | Coffey | |
| 2015/0051725 A1 | 2/2015 | Lee | |
| 2015/0086955 A1* | 3/2015 | Poniatowski | G06T 7/0014 434/262 |
| 2015/0119637 A1* | 4/2015 | Alvarez | A61B 1/0057 600/102 |
| 2015/0180193 A1 | 6/2015 | Sierra et al. | |
| 2015/0287236 A1* | 10/2015 | Winne | G06T 15/08 382/128 |
| 2015/0310601 A1* | 10/2015 | Rodriguez | G07G 1/0072 348/150 |
| 2016/0000516 A1* | 1/2016 | Cheng | A61B 34/20 600/424 |
| 2016/0030134 A1* | 2/2016 | Shapter | A61B 34/25 606/130 |
| 2016/0135762 A1* | 5/2016 | Mihailescu | A61B 6/4241 600/424 |
| 2016/0275703 A1* | 9/2016 | Mariampillai | A61B 5/055 |
| 2016/0324664 A1 | 11/2016 | Piron | |
| 2017/0083115 A1* | 3/2017 | Speck | G02B 27/017 |
| 2017/0215985 A1* | 8/2017 | Kubiak | A61B 90/37 |

(56) References Cited

U.S. PATENT DOCUMENTS

2017/0252112 A1* 9/2017 Crawford ............... A61B 34/32
2018/0055482 A1* 3/2018 Wilcox .................... A61B 8/15
2018/0071032 A1* 3/2018 de Almeida Barreto ....................
                                                         G16H 50/50

OTHER PUBLICATIONS

European Search Report issued in Application No. 16196541.3, dated Feb. 24, 2017.

* cited by examiner

AUTOMATED SYSTEM FOR LASER-ASSISTED DERMATOLOGICAL TREATMENT

CROSS-REFERENCE TO RELATED APPLICATIONS

The present application is a continuation of U.S. application Ser. No. 15/337,112, filed Oct. 28, 2016, which claims the benefit under 35 U.S.C. § 119 of Finnish application No. FI 20155784, filed on Nov. 5, 2015.

FIELD OF THE INVENTION

The present invention generally relates to laser-assisted dermatological treatment systems and methods; more particularly the invention concerns an automated, robot arm assembly based system for laser-assisted removal of tattoos, scars and/or pigmented dermatological conditions from skin and an associated method for controlling thereof.

BACKGROUND

The attempts to remove tattoos date back to the origins of tattooing—creating permanent marks or designs on the body—an ancient practice for identification and/or decoration of an individual, which has been in existence since the early beginnings of modern civilization. Since in recent decades a trend for tattooing became a matter of individual choice to serve the purpose of self-expression, the patients seek tattoo removal on a more frequent and routine basis, accordingly.

Since the present-day tattooing technology involves injection of ink particles into a skin dermis (a layer of skin beneath epidermis) at a depth about 1.1-2.9 mm below the skin surface, removal of a tattoo requires elimination of said pigment from the skin, accordingly. Sophisticated modern laser-assisted methods target the tattoo ink and break it up into smaller particles, which are naturally absorbed by the body's immune system.

Laser-assisted tattoo removal by argon and carbon dioxide lasers has been piloted at 1970s; however, these lasers have caused non-specific ablation of tissue at a tattoo site when targeting water molecules as chromophores and in majority of cases have failed to remove the tattoo completely while leaving scars. Recent techniques utilize quality-switched (QS) lasers, such as an alexandrite, ruby and neodymium:yttrium-aluminum-garnet (Nd:YAG) lasers, for example, capable of producing nanosecond range pulses at very high peak power. Moreover, an apparatus for tattoo removal utilizing lasers with pulse duration in a picosecond range is disclosed in the U.S. Pat. Nos. 7,586,957 and 7,929,579 and in the U.S. patent application publication No. 2015/180193. A device for tattoo removal utilizing a titanium doped sapphire (Ti:Sapphire) solid state laser with pulse duration in a femtosecond range is further disclosed in the U.S. Pat. No. 8,187,256.

The abovementioned laser-assisted devices and systems are still constrained with limitations caused by an ultimate dependence thereof on human factor. In other words, modern technology involves devices and systems for tattoo removal that are all human (manual) operated. In this regard, localization of pigment on a patient's skin and provision of pulses of electromagnetic radiation to remove said pigment are performed by an operator. As a consequence, accuracy, precision, speed and overall efficiency of the treatment are to a certain extent biased by an operator performance error.

Since standardization of manually performed tattoo and/or scar removal procedures in terms of precision vs speed parameters is hampered, the treatment duration is often overextended and the patient is caused to experience unnecessary pain or at least discomfort. The aforesaid applies equally well to other undesirable pigmented dermatological condition (lesions) of varying nature.

If tattooing becomes even more widespread than it is today, the request for tattoo removal will increase exponentially. In this regard, a demand for more effective permanent tattoo removal solutions still exists.

SUMMARY OF THE INVENTION

An objective of the present invention is to at least alleviate one or more problems arising from the limitations and disadvantages of the related art. The objective is achieved by various embodiments of an automated system for laser-assisted dermatological treatment and a method for controlling thereof.

Thereby, in one aspect of the invention an automated system for laser-assisted removal of an undesirable dermatological condition from skin is provided, according to what is defined in the independent claim 1. The system thus comprises a robot arm assembly, comprising an end effector in the form of a laser head coupled to an articulated robot arm and a controlling unit. The system is configured to sequentially direct, via the laser head, laser energy to a number of pre-determined, individual portions of skin identified within the boundaries of a pre-defined skin surface area intended for treatment and at least partly comprising said undesirable dermatological condition, wherein the controlling unit is configured to adjust positioning of the robot arm assembly with respect to each individual skin portion and directing laser energy thereto in real time, said controlling unit is further configured to receive a series of parameter data obtainable from an at least one proximity sensor and an image acquisition device provided within the laser head and, based on said parameter data, to issue a series of updated commands to each of the robot arm and the laser head continuously throughout the treatment.

In one preferred embodiment the system further comprises a processing unit configured to generate and store a virtual model of the pre-defined skin surface area intended for treatment, to identify a number of sub-areas within said model, wherein each sub-area corresponds to the individual skin portion within the boundaries of the pre-defined skin surface area intended for treatment, and to communicate the data on thus identified sub-areas to the controlling unit and/or the robot arm assembly.

The processing unit of the system is preferably configured to update and adjust the stored virtual model based on the series of parameter data received from the controlling unit and/or the robot arm assembly and to communicate thus updated and adjusted model data to the controlling unit and/or the robot arm assembly, wherein updating, adjusting and communicating the model data is executed in real time and continuously throughout the treatment.

In some alternative embodiment the controlling unit is combined with the processing unit.

In some further embodiment the system further comprises a treatment platform for accommodating a patient.

In some embodiment the undesirable dermatological condition to be treated is tattoo. In some other embodiments the undesirable dermatological condition to be treated is selected from the group consisting of: scars, birthmarks, moles, freckles, lentigines, solar lentigo and hyperpigmentation.

In another aspect of the invention a method for real-time controlling an automated laser-assisted removal of undesirable dermatological condition from skin implemented by a system according to the previous aspect is further provided, according to what is defined in the independent claim 12.

In still another aspect a computer program product embodied in a non-transitory computer readable medium and comprising computer code for causing the computer to execute the method according to one of the previous aspects is provided, according to what is defined in the independent claim 14.

The utility of the present invention arises from a variety of reasons depending on each particular embodiment thereof. At first, the system provides for fast and precise removal of the undesirable dermatological condition from skin in an essentially operator-independent manner, thus being free of errors caused by human factor. Any laser-assisted removal of undesirable dermatological conditions from skin inevitably results in ablating also the unaffected skin regions, when performed manually by the operator. For example, upon laser-assisted tattoo removal by hand the operator manually targets laser pulses onto the patient's skin; however, manually directed lasing beam hits, along with the pigmented skin regions, also the ones free of pigment. Even the treatment performed by the experienced personnel is not error-free. By utilization of the system provided hereby this operator performance error related drawback can be completely eliminated.

The system further allows for speeding up the treatment and/or for accomplishing the treatment during a reduced number of sessions as compared to the manual same, thus reducing costs and avoiding unnecessary discomfort.

The term "dermatological condition" is utilized within the present disclosure as a synonym of the term "skin condition".

The expression "a number of" refers herein to any positive integer starting from one (1), e.g. to one, two, or three.

Different embodiments of the present invention will become apparent by consideration of the detailed description and accompanying drawings.

DETAILED DESCRIPTION OF THE EMBODIMENTS

Figure 1:
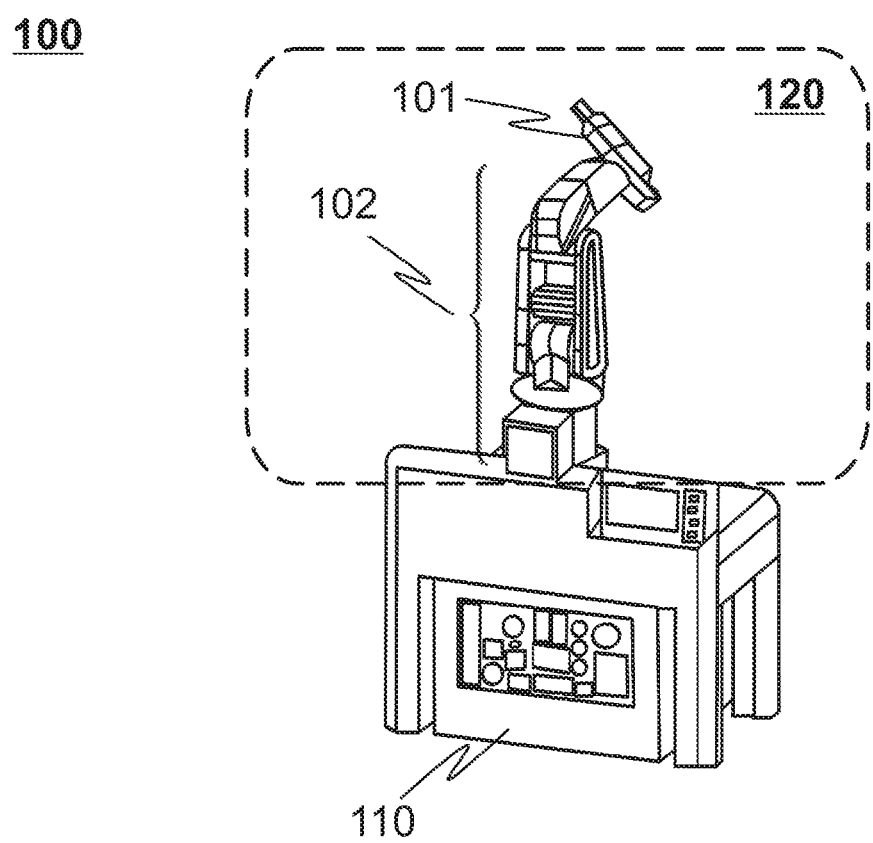
FIG. 1 is a perspective view of an automated system 100 for automated laser-assisted dermatological treatment in accordance to some aspect of the invention.

Detailed embodiments of the present invention are disclosed herein with the reference to accompanying drawings. The same reference characters are used throughout the drawings to refer to same members. Following citations are used for the members:

100—an automated system for laser-assisted dermatological treatment;
101—a laser head;
102—a robot arm, wherein: 102*a* is a base; 102*b* is an upper arm and 102*c* is a forearm;
103*a-c*—joint connectors, wherein: 103*a* is a shoulder hinge; 103*b* is an elbow hinge; and
103*c* is a rotary joint at the forearm;
104—a rotatable joint adapter/mounting means for the laser head;
105*a*, 105*b*—communication lines between the control unit and the robot arm and between the control unit and the laser head, respectively;
110—a controlling unit;
111—a processing unit (a computer);
120—a robot arm assembly
201—a treatment platform;
202—stairs (auxiliary appliance);
203—a supporting rack (auxiliary appliance);
204—wheels for the supporting rack (auxiliary appliance);
210—a patient;
301—a casing (laser head);
302—a lasing beam aperture;
303—an image acquisition device and proximity sensor(s);
304—a fastening element;
305—a cable port;
310—a lasing beam;
410—an undesirable dermatological condition to be treated;
501—a skin surface area intended for treatment;
501*a*—an individual skin portion within the area 501;
502—a virtual field model of the area 501;
503—a grid;
504—a sub-area within the model 502 corresponding the skin portion 501*a*.

FIG. 1 illustrates at 100 the concept underlying various embodiments of an automated system for laser-assisted dermatological treatment in accordance with some aspect of the present invention. In preferred embodiment the laser-assisted dermatological treatment comprises removal of an undesirable dermatological condition from skin. In the most preferred embodiment the undesirable dermatological condition is tattoo.

In some other embodiment the undesirable dermatological condition is a scar. The scar to be treated may be caused by any of an accident, infection, inflammation or surgery. In further embodiments, the undesirable dermatological condition is a pigmented dermatological condition (lesion), selected from the group consisting of birthmarks, moles, freckles, lentigines, solar lentigo and various types of hyperpigmentation.

By the term "automated" we refer in the present disclosure to the system, configured to perform the laser-assisted dermatological treatment comprising removal of an undesirable dermatological condition from skin essentially in an absence of human attendance. By the term "essentially" we stipulate that, although the system is configured to perform all actions related to the treatment per se in an absence of human attendance, presence of an operator is still required for inputting patient related data and/or spatially adjusting systems' gear with regard to a patient and a skin surface area intended for treatment, accordingly. Presence of the operator is still highly desirable throughout the entire treatment for safety purposes.

The system, according to one aspect, is thus configured to combine and/or to synchronize system data comprising pre-determined and/or pre-selected system parameter settings, and patient-related data comprising parameter data related to the undesirable dermatological condition intended for treatment and obtainable prior to and throughout the treatment.

Figure 2A:
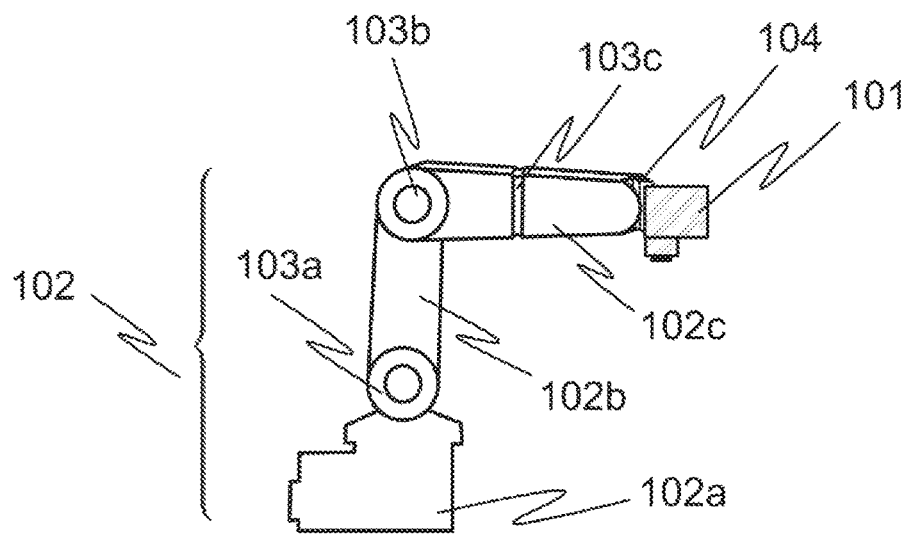
FIG. 2A is a schematic view of a robot arm assembly 120 provided within the system 100.

The system 100, according to one basic embodiment, comprises a robot arm assembly 120 and a controlling unit 110 (FIG. 1). The robot arm assembly 120 comprises an articulated robot arm 102, having an end effector configured as a laser head 101. The laser head 101 is therefore coupled to the articulated robot arm 102. The robot arm 102 is preferably implemented as a tabletop or otherwise an essentially small-sized robot arm manipulator having a number of segments interconnected by means of hinged joints to a kinematic chain. The height of the robot arm 102 when fully extended is about 500-1500 mm. In one exemplary embodiment (FIG. 2A) the robot arm 102 comprises a base 102a, an upper arm 102b supported at one end on the base 102a by means of a shoulder hinge 103a and a forearm 102c pivoted to the other end of the upper arm 102b by an elbow hinge 103b. The forearm 102c is further separated into two sub-segments by a rotary joint 103c and comprises a rotatable joint adapter 104 at its free end configured to receive the laser head 101. The rotatable joint adapter 104 thus forms a mounting means for the laser head 101. The laser head 101 is mounted onto the forearm 102c by means of aforesaid rotatable joint adapter 104, accordingly.

Figure 2B:
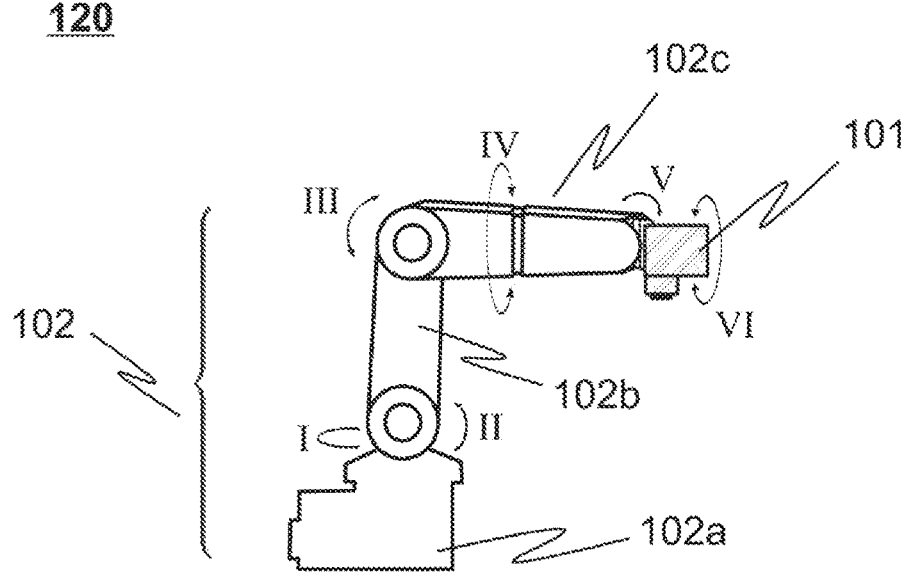
FIG. 2B illustrates rotational axes of the assembly of FIG. 2A.

The robot arm assembly 120 is preferably configured to have at least six degrees of freedom, indicated on FIG. 2B by roman numerals I-VI. In the assembly 120 shown on FIG. 2B the upper arm 102b, supported on the base 102a, is thus configured to rotate about its longitudinal axis (I) and to heave forward and backward (axis II) relative to the shoulder hinge 103a, whereas the corresponding forearm 102c is configured to perform the heaving motion relative the elbow hinge 103b (axis III). The rotary joint 103c further ensures rotational movement of a distal sub-segment of the forearm 103c about its longitudinal axis (IV). By the distal sub-segment we refer to the sub-segment of the forearm 103c connectable via the adapter 104 to the laser head 101. The laser head 101 is further arranged to rotate about at least two orthogonal axes (herein V, VI) by means of the rotatable joint adapter 104.

Aforementioned rotational axes are given by way of example, not limitation; therefore, the robot arm 102 and the assembly 120 may be embodied as having higher degrees of freedom by implementing any or both of the robot arm segments 102b, 102c to extend telescopically, by providing different and/or additional rotational axes for joint connectors 103a-c and 104 and/or by mounting the assembly 120 on tracks. Movements of the robot arm segments 102b, 102c and of the laser head 101 relative to each associated axis are realized by suitable motors, typically servo motors. The robot arm 102 may additionally comprise a variety of built-in sensors, such as torque-, pressure- and motion sensors, compensators, wire harnesses, cables and feeds, a power supply and any other components essential for the purposes of the present invention.

Figure 3:
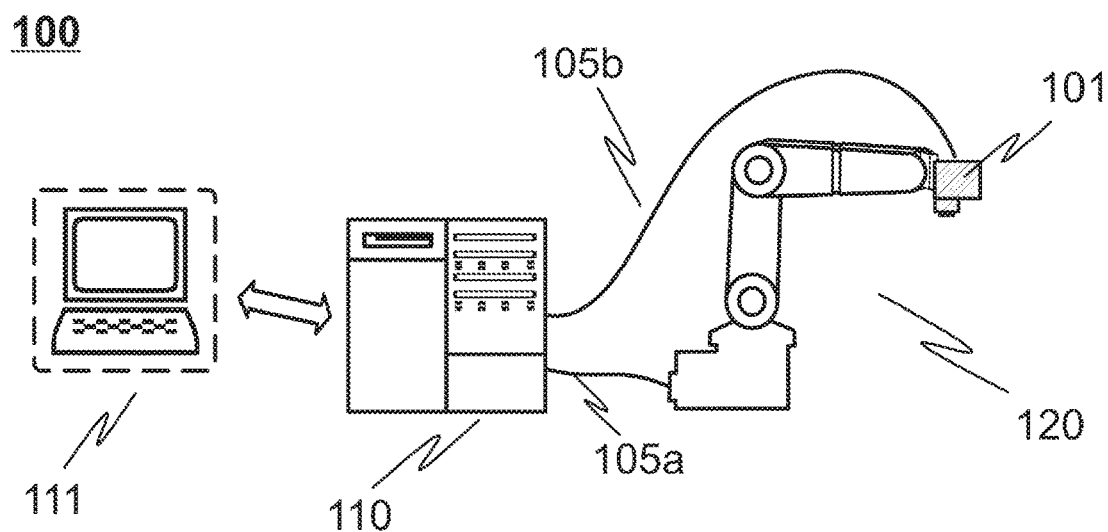
FIG. 3 is a schematic view of the system 100.

The system 100 according to another preferred embodiment is illustrated by FIG. 3, said system 100 further comprising a processing unit 111 implemented as a computer workstation, such as a tablet computer, a portable computer, a mobile electronic device and the like. The processing unit 111 may be further configured as a remote server workstation being in communication with the controlling unit 110 and/or the robot arm assembly 120 via wired and/or wireless connection. In the embodiment shown on FIG. 3 the controlling unit 110 and the processing unit 111 are provided as discrete devices interconnected by a number of wired and/or wireless communication lines (schematically shown by arrow). In some alternative embodiment the controlling unit 110 and the processing unit 111 may be combined within a single device.

The controlling unit 110 is implemented to execute direct controls over the robot arm assembly 120 and therefore comprises at least mechanical (motion) controllers for the robot arm 102, laser function controllers for the laser head 101, and a controlling means for integrating and coordinating functions of the laser head 101 with that of the robot arm 102. The controlling unit 110 preferably comprises a laser source unit, power supply/supplies, motors, circuit boards, programmable logic controllers, control relays, drives, a cooling fan and a number of cable connectors/ports. The controlling unit 110 further comprises a front-panel control module (a user interface) and an associated circuitry. The front-panel control module may be realized as a graphical user interface (GUI) in the form of a display screen, preferably a touchscreen; as a control panel with a number of manual switches and an at least one monitoring panel/display screen; or as a combination thereof.

The controlling unit 110 is configured to communicate with the robot arm 102 via a communication line 105a; and with the laser head 101—via a communication line 105b (FIG. 3). Said communication lines 105a, 105b are advantageously configured to comprise power transmission cables, connecting each of the robot arm 102 and the laser head 101 to the appropriate power source. The communication line 105a further comprises a signal communication line provided in the form of a fiber optic cable, for example, and configured to transfer data on commands issued and/or mediated by the controlling unit 110 to the robot arm 102 for activating motion control mechanism(s) thereof and to receive feedback data, accordingly. The communication line 105b further comprises lasing beam delivery system, configured to deliver lasing beam from the power source (laser source), provided within the controlling unit 110 or separately therefrom, to the laser head 101. The lasing beam delivery system is advantageously configured as a fiber optic cable assembly, further comprising an input- and output coupling optics and a number of connectors, adapters and the like. It is advantageous that one end of the fiber optic cable is permanently attached to the laser source whereas the opposite end of the cable includes a beam collimator and isolator enclosed into the laser head 101

The laser head 101 connected by means of the communication line 105b to the laser source unit, advantageously provided within the controlling unit 110, and the aforementioned laser source unit form a laser module within the system 100. Selection of laser for the laser module is on one hand predetermined by an energy source (a pump source) and a gain medium, and on another hand, is object-related, i.e. dependent on the type of the undesirable dermatological condition intended for treatment, since successful treatment is largely anticipated by a wavelength of light emitted by laser.

In one preferred embodiment a Nd:YAG laser is utilized. The laser module is preferably configured as a Q-switched (QS) Nd:YAG laser capable of working in regimes of short pulses (in microsecond range) and/or ultra-short pulses (in nano- and picosecond ranges and shorter). Alternatively a Nd:YAG laser capable of producing light energy pulses in millisecond range may be utilized. In another preferred embodiment a so called frequency-doubled QS Nd:YAG laser, comprising, along with the Nd:YAG crystal, also a potassium titanyl phosphate (KTP) crystal, it utilized. While the common Nd:YAG lasers emit at 1064 nm (infrared), the aforesaid frequency doubled Nd:YAG lasers are capable of emitting at two wavelengths, namely, at 1064 nm and at 532 nm, wherein the latter wavelength (green) is produced by doubling the frequency of 1064 nm laser light by the KTP crystal. Laser emission at 1064 nm enables successful treatment of most frequently utilized dark tattoo pigments, such as black and dark-blue, whereas brown, red, orange, and some yellow pigments can be treated using the 532 nm wavelength. Moreover, since it is known that light absorption by epidermal melanin pigment at 1064 nm is less high than that at 694 nm produced by QS ruby laser and at 755 nm produced by QS alexandrite laser, utilization of QS Nd:YAG lasers reduces various skin alterations and/or scarring, especially upon treating patients with darker skin.

However, in order to treat other tattoo color formulations, such as green and blue, for example, additional and/or alternative utilization of other lasers, such as a QS Ruby laser emitting at the 694 nm and a QS Alexandrite laser emitting at the 755 nm, is not excluded.

Other important parameters to be determined and/or selected prior the treatment include laser power, intensity, fluence, pulse duration, pulse frequency, a number of pulses per a unit of time, as well as a spot size/diameter selected for treatment (in order to avoid treating surrounding unaffected area to minimize pigmentary alterations).

Figure 4:
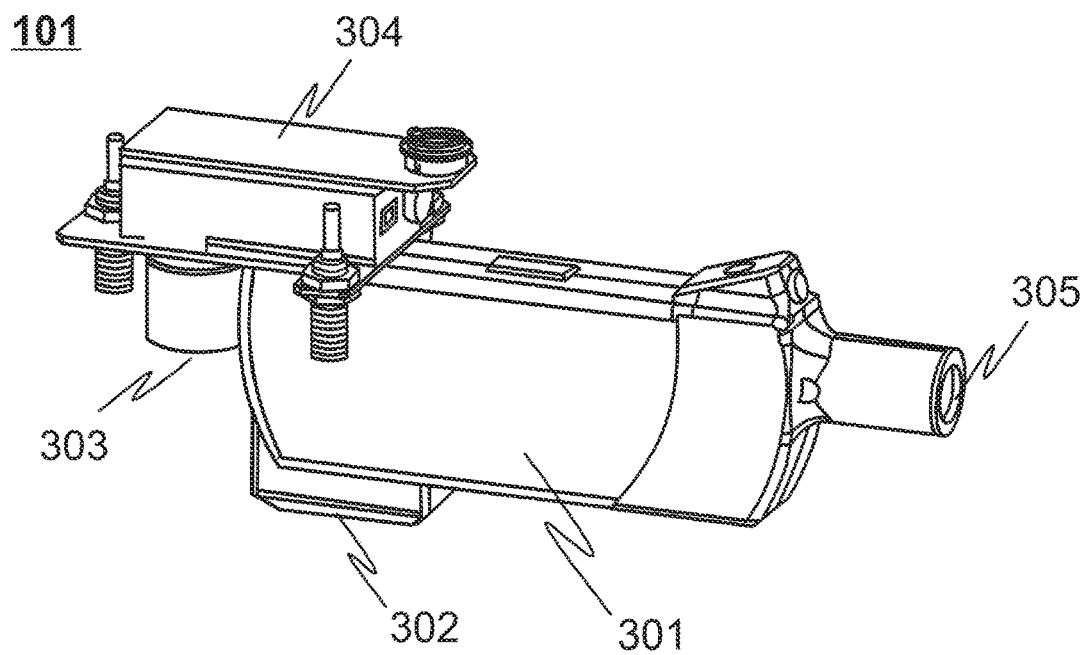
FIG. 4 shows is a perspective view of a laser head provided within the assembly 120 and the system 100, accordingly.

Reference is further made to FIG. 4 illustrating the laser head 101. The laser head 101 thus comprises a casing 301, having an aperture 302 for a lasing beam and a cable port 305 for receiving the communication line 105b, which connects the laser head 101 to the laser source (provided within the controlling unit 110, for example). Fixation of the laser head to the robot arm 102 and, in particular, to the joint adapter 104 thereof, is implemented by means of a fastening element 304. Connections of the laser head 101 to the laser source and to the robot arm 102 mediated by the cable port 305 and the fastening element 304, accordingly, can each be either permanent or detachable. In some embodiment the laser head 101 is permanently connected to the laser source and detachably—to the robot arm.

The laser head 101 further comprises an at least one image acquisition device and an at least one proximity sensor. The image acquisition device is preferably a color camera utilizing CCD (semiconductor charge-coupled device), CMOS (complementary metal-oxide-semiconductor) or NMOS (N-type metal-oxide-semiconductor) technologies. The proximity sensor(s) may be any of the inductive, capacitive, photoelectric or ultrasonic sensors. Laser sensor(s) or ultrasonic sensor(s) may still be preferred. In the embodiment shown on FIG. 4 the camera and the proximity sensor(s) are provided within an appliance 303. In some embodiment the sensor(s) may be integrated with the camera. The appliance 303 can be incorporated or fixed to the casing 301 or the fastening element 304. Alternative configurations are possible (not shown), in which the camera and the proximity sensor(s) are disposed apart from each other.

In one preferred embodiment the laser head 101 comprises three proximity sensors, preferably solid-state sensors, located at a certain distance from each other to form a triangle. A "three-point" measurement implemented via the aforesaid configuration ensures correct alignment of the laser head 101 with respect to a predetermined point at skin surface area intended for treatment and allows to overcome errors caused by skin irregularity and degree of curvature.

Figure 5A:
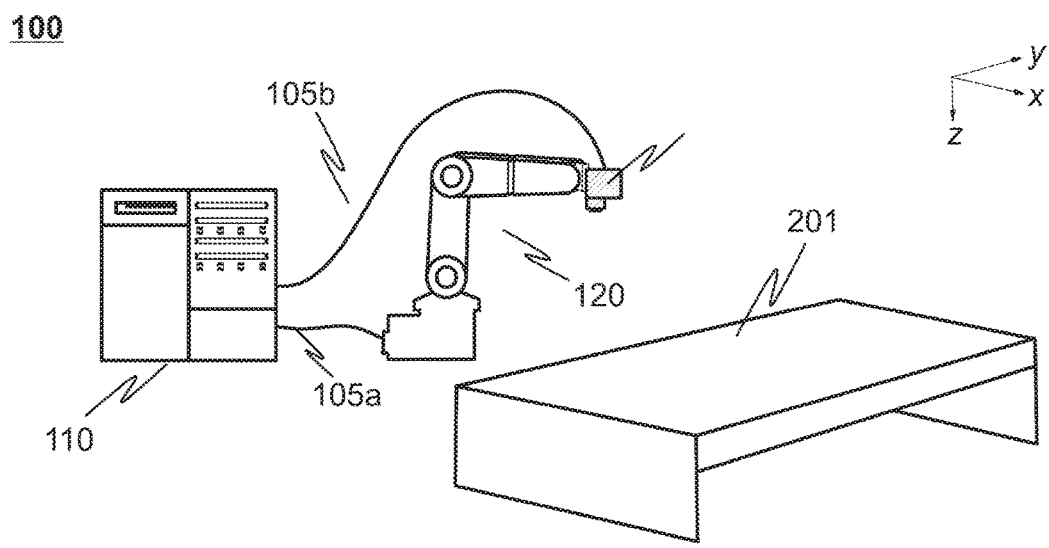
FIGS. 5A and 5B show a schematic view and a perspective view, accordingly, of the system 100 implemented according to some embodiment.
Figure 5B:
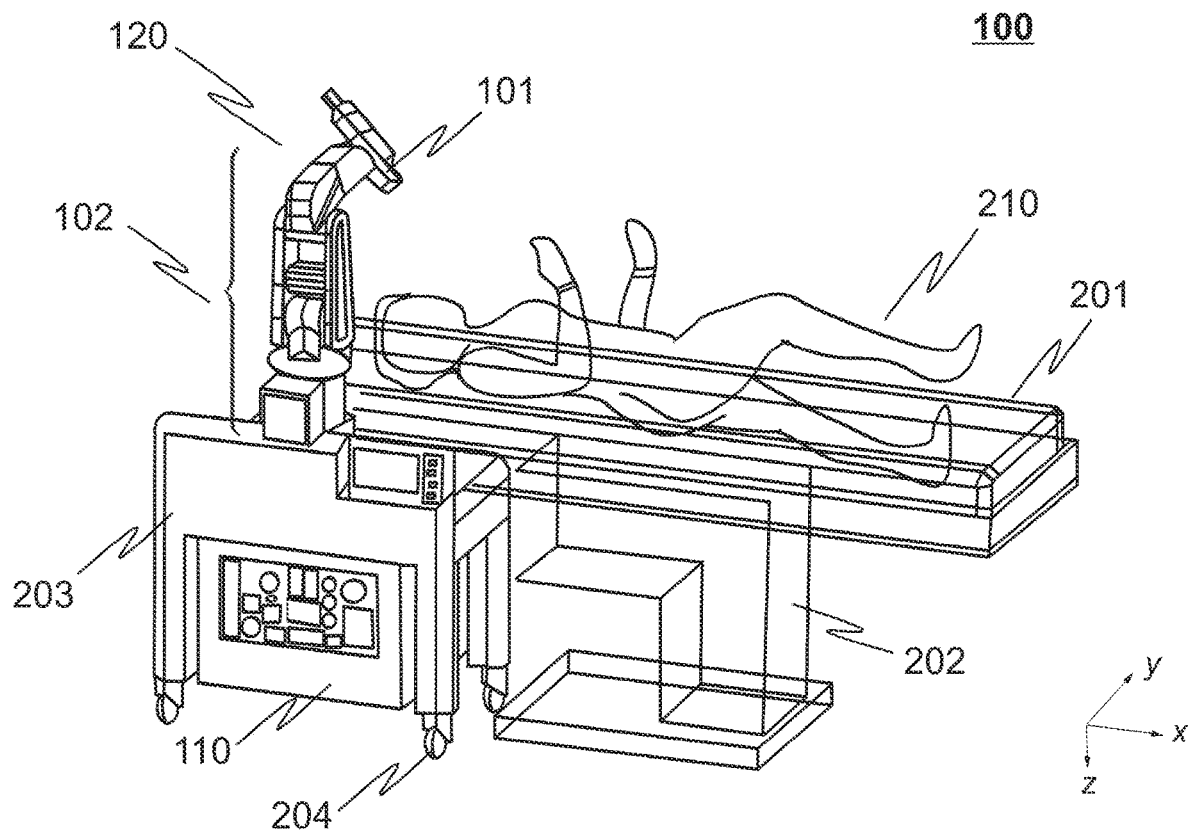

Reference is further made to FIGS. 5A and 5B illustrating the system 100 according to some other embodiment. According to the embodiment shown on FIGS. 5A and 5B the system 100 further includes a treatment platform 201 for accommodating a patient 210 thereon (FIG. 5B). It should be noted that the system shown on FIGS. 5A and 5B may additionally include the processing unit 111 (not shown) either independently or as a part of the controlling unit 110. The treatment platform 201 may further include auxiliary appliances (FIG. 5B), such as stairs 202 and/or wheels (not shown), whereas the robot arm assembly 120 may be further mounted onto a rack 203. The embodiment of FIG. 5B shows a configuration, in which the rack 203 provides a support for both the robot arm assembly 120 and the controlling unit 110. The rack 203 may further be rendered movable by provision of wheels 204. Any other mounting means capable of providing sufficiently stable support for the robot arm assembly 120 and/or the controlling unit 110 may be alternatively utilized.

In some embodiment the treatment platform 201 may be provided separately from the rack 203, therefore the rack 203 may be freely driven around the treatment platform 201. In some other embodiments the treatment platform 201 and the rack 203 are attached to each other by means of guiding rails, for example, in order to enable sliding or rolling movement of the rack 203 along the edge of the treatment platform 201. The guiding rails are advantageously provided with a locking means (not shown) in order to preclude accidental movements of the rack 203 during the treatment. The treatment platform 201 may, in turn, be implemented as a flat bed, an adjustable bed or a chair. An adjustable bed, with an at least one folding point in the middle and both ends being adjustable in vertical direction, is preferred. Such configuration is especially advantageous when the rack 203, hosting the robot arm assembly 120, is fixed to the treatment platform 201 by means of the abovementioned guiding rails, for example, since it allows treating either side of the patient's body (e.g. right and left arms) without disengaging the rack 203 and the treatment platform 201 from each other. Aforesaid configurations are given by way of example only; for those skilled in the art it is evident that other configurations, in view of design, realization and disposition of the treatment platform 201, the rack 203 and the auxiliary appliances 202, 204, are possible.

Figure 6:
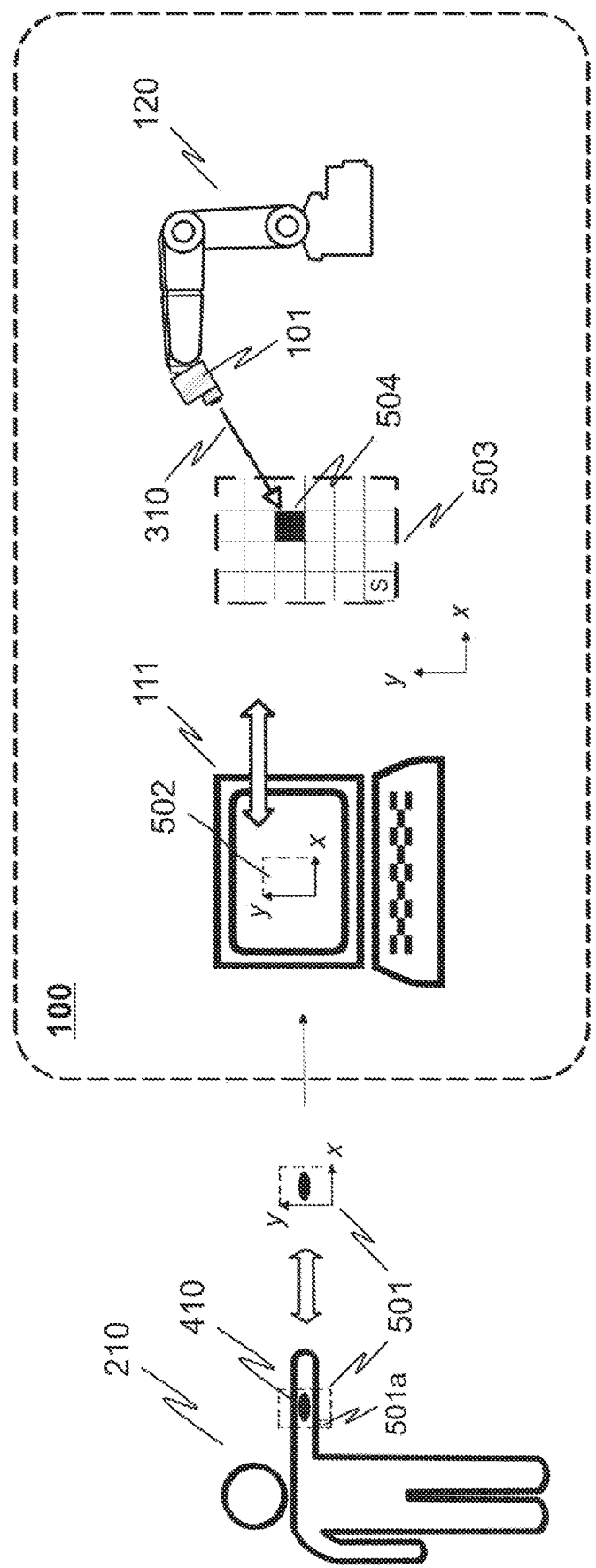
FIG. 6 schematically illustrates a process for the automated laser-assisted dermatological treatment mediated by the system 100.

The operation principle of the system 100 will be further described in more detail with reference to FIG. 6. The dotted-line box on FIG. 6 is herewith indicative of the system 100 being automated according to the definition above, i.e. defines a scope of actions executable by the system 100 throughout the treatment per se and in an absence of human attendance. For clarity purposes the treatment per se may be specified as a sequence of actions performed by the system 100 since a data on a skin surface area 501 intended for treatment and at least partly comprising an undesirable dermatological condition 410 has been input into the processing unit 111 or, in an absence of a distinct processing unit into the controlling unit 110 or a combination thereof, till the moment the robot arm assembly 120 has acquired a final position after having worked the entire area 501.

Prior to the treatment an operator (a physician, a medical attendant etc.) switches on the system 100 and brings the robot arm assembly 120 into a sufficient proximity to the patient 210 and the undesirable dermatological condition 410 to be treated. As described above the robot arm assembly 120 may be mounted onto a movable rack further incorporating the controlling unit (not shown). The operator further defines the area 501 intended for treatment on patient's skin surface. The area 501 may be defined by drawing straight lines in x and y directions around or within the dermatological condition 410, with or without a reference mark, and measuring length and width of a rectangular thus obtained. In the example shown on FIG. 6 the area 501 is therefore rectangular and entirely incorporates the condition 410. In some particular instances the operator may define the shape of the area 501 as being other than rectangular, such as square, triangular, circular and the like, whether appropriate. Also more complex shapes are not excluded. In some other instances the area 501 may not necessarily incorporate the entire condition 410; therefore, in case of large and very large dermatological conditions to be treated, such as large tattoos, for example, the operator may have to determine the area 501 within the dermatological condition 410, in which case the area 501 includes the condition 410 only partly.

The operator further inputs measured parameters and other patient-related data into the processing unit 111. Patient-related parameters may thus be selected from the group consisting of: dimensional parameters, such as length, width, diameter, radius etc., of the skin surface area 501 intended for treatment, skin color, type of the dermatological condition and a pigment color, whether the dermatological condition is tattoo. Mentioned parameters may be input manually or at least partly automatically, by means of photographing the dermatological condition 410 intended for treatment, for example. The operator further inputs and/or adjusts laser parameters, such as power, pulse duration, spot diameter, pulse frequency, a number of pulses per a unit of time, and optionally a wavelength. Further operational stages are advantageously performed by the system 100 in an operator-independent manner.

Based on the patient-related parameter data input into the processing unit 111 a virtual field model 502 is created. The model 502 constitutes a two-dimensional representation of the skin surface area 501, whose boundaries are determined by virtual axes x and y, corresponding to length and width of the skin surface area 501. Parameters for grid 503 formation are further determined. Upon grid formation the model 502 is split into a number of sub-areas 504, preferably equal-sized, further referred to as squares. In one preferred embodiment the size of each sub-area 504 is about 1 square inch (1"×1") or 25.4 mm$^2$. Dimensional calculations for each square 504 include the amount of spatial deviation intended to correct errors caused by skin surface irregularities and/or degree of curvature. In fact, each square 504 in the grid 503 comprises a border edge by which extent it overlaps with the neighboring squares. Dimensions of such overlapping edges ("joint seams") can be standardized or determined case-wise. In practice, width of the border edge around each individual square 504 may vary within a range of 10-25% with respect to the width of a single square, thus constituting 0.1-0.25 inch (2.5 mm-6.35 mm). The data on the field model 502 and the grid 503 is stored in the memory of the processing unit 111.

Data on thus formed grid 503 is further communicated to the controlling unit 110 (not shown), in which said data is transformed to a number of commands for the robot arm assembly 120. The robot arm assembly 120 is further configured, by means of the proximity sensors provided in the laser head 101, to estimate a starting position of the laser head 101 with regards to the skin surface area 501 based on the virtual model 502 and the grid 503. The skin surface area 501 intended for treatment may thus be considered as comprising a number of individual portions 501a, each portion 501a corresponding to a related virtual sub-area 504. Determination of the starting position includes selection of a "first" virtual sub-area 504 and selection of a certain location therewithin (i.e. corner or center) and further acquisition of a starting point within the related skin portion 501a, corresponding to said "first" sub-area 504. As an exemplary first sub-area, indicative of a starting position hereby, a square at the lower left corner of the grid 503 may be selected (marked by a capital "S", FIG. 6). The starting position of the laser head 101 with regards to each subsequent virtual sub-area 504 and the related skin portion 501a, accordingly, may be determined in the same manner.

Selection of a starting position within the virtual model 502 and selection of the directions along x and y axes for a "row-wise" movement of the robot arm 201 carrying the laser head 101 may be pre-programmed; however manual input, selection and/or modification thereof is preferably made available. The laser head 101 is then positioned such that lasing beam trajectory would form an essentially right angle with an imaginary line on the skin surface it falls onto. The term "essentially right angle" is used in the present disclosure to indicate an angle formed between a lasing beam and a skin surface being within a range of 60° to 90°. Acquisition of a starting point, i.e. of a point within the skin portion 501a, corresponding to the "first" virtual sub-area 504 ("S"), and within each subsequent skin portion includes positioning of the laser head 101 with regard to each of said skin portions, implemented preferably by means of three distinct solid state proximity sensors, as disclosed above, in order to attain a "three-point" measurement. However, in case the dermatological condition 410 is very small, such as a small tattoo located on a finger, for example, proximity measurement(s) may be omitted.

After the laser head 101 has been aligned with respect to the aforesaid starting point within the skin portion 501a corresponding to the "first" virtual sub-area 504 ("S"), an image of said skin portion 501a is acquired by means of the image acquisition device, such as a color camera, provided within the laser head 101. Thus, each individual skin portion 501a being captured at a time by the image acquisition device corresponds to a single virtual square 504 and constitutes 1 square inch (1"×1"). Upon capturing individual skin portions 501a the image acquisition device is preferably adjusted to additionally include the abovementioned spatial deviation correction data.

Proximity measurement data obtained by the proximity sensor(s) and data on captured images obtained by the image acquisition device, such as a color camera, for each individual skin region 501a are transmitted to the controlling unit 110 and/or the processing unit 111 for processing and reconstruction of the dermatological condition 410 within the virtual field model 502 and the grid 503. During reconstruction it is preferably monitored to which extent the images obtained from each skin portion 501a overlap with each other; the overlapping edges are further removed automatically by means of an appropriate computer program product, according to some further aspect of the invention.

Once reconstruction is complete the processing unit 111 is configured to issue a "START" command for initiating a series of actions performed by the robot arm assembly 120 and resulting in the removal of the dermatological condition 410 within the pre-defined skin surface area 501. In particular, the robot arm 102 is set to the starting position ("S") and laser supply from the laser source to the laser head 101 is initiated. The command(s) issued by the processing unit 111 are advantageously mediated by the controlling unit 110. The system 100 is preferably configured to notify the personnel and the patient by a sound signal, for example, on its readiness for starting laser supply onto skin. Sound notification may be issued by the processing unit 111 and/or the controlling unit 110, accordingly. In some embodiments the lasing beam delivery onto skin after issuing a notification may be initiated automatically, within a predetermined time period (e.g. 30 sec after notification). In some other embodiments the system 100 may be configured to request confirmation for the start, optionally password-protected.

Upon receiving the "START" command the robot arm assembly 120 acquires the starting position ("S") and laser supply to the laser head 101 is therefore initiated. Directing of the lasing beam towards the dermatological condition 410 (FIG. 6) follows the same principles as described above with respect to proximity measurements and image capturing of the individual skin portions 501a. Laser ablation is thus executed square-wise in accordance with proximity and image data obtained beforehand. FIG. 6 schematically illustrates an event of laser ablation occurring within the individual skin portion 501a, provided herewith as a "projection" of the virtual sub-area 504 (black square), by means of the lasing beam 310 emitted by the laser head 101 (for clarity purposes the actual skin portion 501a is omitted from the schematics of laser ablation visualization).

Throughout the laser-assisted treatment of the dermatological condition 410 conducted within each individual skin portion 501a, the proximity sensor(s) and/or the image acquisition device provided within the laser head 101 are configured to continuously execute real-time proximity measurements and/or to acquire digital images, accordingly, of skin surface within each skin portion 501a with predetermined frequency and in predetermined timeframe. Thus obtained data is continuously transmitted to the controlling unit 110 and/or the processing unit 111 for real-time processing. During processing the parameters for the virtual field model 502 and the grid 503 are updated, adjusted and communicated back to the robot arm assembly 120 via the controlling unit 110 or directly. The robot arm assembly 120 is configured, in response to the updated command received from the controlling unit 110, to adjust the position of the robot arm 102 and/or the laser head 101 with respect to the individual skin portion 501a being treated. A feedback loop control over the robot arm assembly 120 is thus implemented.

The laser-assisted treatment of the dermatological condition 410 at least partly comprised within the boundaries of the pre-defined skin surface area 501 is completed when all individual skin portions 501a defined within said area 501 have undergone laser ablation.

As a consequence of the above-described "square-wise" approach and continuous, real-time updating of the individual skin portions' 501a related parameters, the lasing beam can be directed throughout the dermatological condition 410 within the predetermined area 501 with an extremely high precision. The approach additionally allows for avoiding ablation of pigment-free skin surface areas.

According to some other embodiment the system 100 may be configured to proceed directly to the laser-assisted removal of the dermatological condition 410 having the steps of preliminary obtaining a series of parameters data for each individual skin portion 501a via the proximity sensor(s) and the image acquisition device omitted from the laser-assisted treatment. In such an embodiment obtaining the parameter data from each individual skin portion 501a, directing laser energy thereto and issuing a series of updated commands to the robot arm assembly 120 based on said parameter data is executed simultaneously for each individual skin portion 501a.

Additionally or alternatively, the system 100 may require indicating, by a marker, for example, of an at least one reference point on patient's skin. The reference point may thus be used for determination and/or acquisition of the starting point ("S") as disclosed above, and for adjusting positional data during laser ablation within each individual skin portion 501a.

The system 100 preferably comprises manual ON/OFF switch control(s) and PAUSE control(s) and/or an emergency ON/OFF switch control for the entire system 100 and/or each of the laser supply, the robot arm assembly 120, the controlling unit 110 and the processing unit 111.

Figure 7:
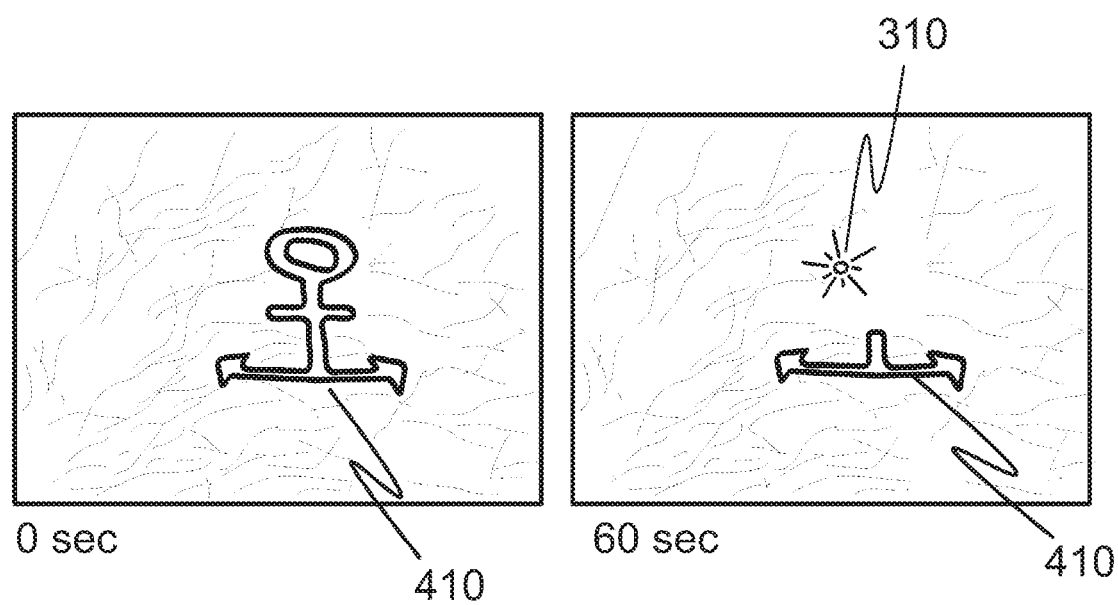
FIG. 7 shows a comparative example for tattoo removal from patient's skin executed by the system 100; the photograph on the left shows a tattoo at the beginning of the treatment (0 sec) and the photograph on the right—the same tattoo 60 sec later.

An exemplary laser-assisted treatment executed by the system 100 is illustrated by FIG. 7, said treatment being a tattoo removal. Figure on the left shows the undesirable dermatological condition 410, being a tattoo, prior to treatment, and figure on the right shows the same during the course of the treatment (60 seconds from the beginning). Size of the tattoo 410 being treated is about 2×3 cm. Based on FIG. 7 one can ascertain that, additional of being highly precise, the laser-assisted tattoo removal executed by the system 100 is times faster when compared to that manually performed by the operator.

In another aspect of the invention a method for operating and real-time controlling the automated system 100, with a robot arm assembly including a laser head coupled to an articulated robot arm, a controlling unit and a processing unit, for laser-assisted removal of undesirable dermatological condition from patient's skin is provided. The method comprises at least the following steps:

a. Generating and storing a two-dimensional virtual model 502 of a pre-defined skin surface area 501 to be treated, including a sub-step of identifying a plurality of sub-areas 504 within said model 502 arranged into a grid, each sub-area 504 corresponding to an individual skin portion 501a within the boundaries of the pre-defined skin surface area 501 to be treated, and issuing a series of commands to the robot arm assembly 120 to acquire a starting position with respect to the surface area 501 to be treated.

b. For each individual skin portion 501a obtaining a series of parameter data by means of at least one proximity sensor and an image acquisition device provided within the laser head 101.

c. Directing, via the laser head 101, laser energy to each individual skin portion 501a.

d. Based on the parameter data obtained at step (b) issuing a series of updated, in real time, commands to each of the robot arm 102 and the laser head 101 continuously during executing step (c) for each individual skin portion 501a.

e. Repeating steps (c) and (d) for each individual skin portion 501a within the pre-defined skin surface area 501.

15. A computer program product embodied in a non-transitory computer readable medium having computer code stored thereon that, upon execution by a computer, causes the computer to execute the method items of claim 13.

In some embodiment the method is configured such that the steps (b), (c) and (d) are executed simultaneously within each individual skin portion 501*a*.

In some further aspect a computer program product is provided, said computer program product being embodied in a non-transitory computer readable medium having computer code stored thereon that, upon execution by a computer causes the computer to execute the method items of the previous aspect. A computer is advantageously the processing unit 111, according to the definition hereinabove. A computer program, also referred to as a program, software, software application, or code, can be written in any form of programming language, including compiled or interpreted languages, and it can be provided in any form, including a standalone program, a module, a component, a subroutine or any other unit suitable for use in a computing environment. A computer program can be configured to be executed on one computer or on multiple computers at one site or distributed across multiple sites and interconnected by a wired or wireless communication network.

It is clear to a person skilled in the art that with the advancement of technology the basic ideas of the present invention are intended to cover various modifications and equivalent arrangements included in the spirit and the scope thereof. The invention and its embodiments are thus not limited to the examples described above; instead they may generally vary within the scope of the appended claims.

The invention claimed is:

1. An automated system for laser-assisted removal of a dermatological condition from skin, the system comprising:
   a robot arm assembly, including a robot arm, and a laser head with an image acquisition device and at least one proximity sensor, said laser head coupled to the robot arm and configured to emit a laser beam to remove the dermatological condition;
   a processing unit, with a memory in communication therewith, that generates and stores a virtual model of a skin surface area of a patient to be treated, based on pre-input patient-related data stored in the memory, the skin surface area to be treated including the dermatological condition to be removed,
   said virtual model comprising a two-dimensional representation of the skin surface area to be treated, the two-dimensional representation including a plurality of equal-sized sub-areas arranged into a grid, each sub-area of said sub-areas corresponding to an individual skin portion of the skin surface area to be treated,
   a size of each sub-area of the virtual model and each corresponding individual skin portion of the skin surface area to be treated being one square inch, and
   the processing unit further configured to perform dimensional calculations for each sub-area of the virtual model, including an amount of spatial deviation for correcting errors caused by skin surface irregularities and/or a degree of curvature of the skin surface area to be treated; and
   a controlling unit that issues a series of real-time feedback-based commands to the robot arm assembly, based on said virtual model, based on a series of parameter data which the controlling unit is configured to receive from the at least one proximity sensor, and based on the image acquisition device for each individual portion of skin defined within the boundaries of the skin surface area to be treated.

2. The automated system of claim 1, wherein the controlling unit is configured to issue the series of real-time feedback-based commands to the robot arm assembly continuously throughout treatment of the skin surface area, so as to cause the robot arm assembly to adjust a position thereof such that the laser head applies laser energy sequentially to each individual portion of skin defined within the boundaries of the skin surface area to be treated.

3. The automated system of claim 1, wherein the processing unit is further configured to update and adjust the stored virtual model, including the grid, based on real-time feedback data that the processing unit is configured to receive from at least one of the controlling unit and the robot arm assembly, and to communicate data of said updated and adjusted virtual model to at least one of the controlling unit and the robot arm assembly continuously throughout the treatment.

4. The automated system of claim 1, wherein the controlling unit is combined with the processing unit.

5. The automated system of claim 1, wherein the laser head includes therein three proximity sensors disposed at a pre-determined distance from each other.

6. The automated system of claim 1, wherein the laser head includes an Nd:YAG laser.

7. The automated system of claim 1, further comprising: a treatment platform for accommodating the patient.

8. The automated system of claim 1, configured for laser-assisted removal of a tattoo.

9. The automated system of claim 1, configured for laser-assisted removal, from the skin surface area to be treated, of any selected from the group consisting of: scars, birthmarks, moles, freckles, lentigines, solar lentigo, and hyperpigmentation.

10. The automated system of claim 1, wherein the image acquisition device of the laser head is a camera.

11. The automated system of claim 1, wherein the pre-input patient-related data is selected from the group consisting of: dimensional parameters of the skin surface area to be treated that includes the dermatological condition for removal, a skin color, a type of said dermatological condition, and a pigment color of said dermatological condition.

* * * * *